(12) United States Patent
Sohn

(10) Patent No.: US 6,407,305 B1
(45) Date of Patent: Jun. 18, 2002

(54) ADSORPTIVE SEPARATION PROCESS FOR RECOVERY OF TWO PARAFFIN PRODUCTS

(75) Inventor: Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/671,219

(22) Filed: Sep. 27, 2000

(51) Int. Cl.⁷ ................................................. C07C 7/12
(52) U.S. Cl. .................. 585/820; 585/825; 585/826; 585/822
(58) Field of Search .................. 585/820, 822, 585/825, 826

(56) References Cited

U.S. PATENT DOCUMENTS

| | | | |
|---|---|---|---|
| 2,477,382 A | 7/1949 | Lewis | 260/671 |
| 3,205,166 A | 9/1965 | Ludlow et al. | 208/310 |
| 3,510,423 A | 5/1970 | Neuzil et al. | 208/310 |
| 4,006,197 A | 2/1977 | Bieser | 260/676 MS |
| 4,036,745 A | 7/1977 | Broughton | 208/310 |
| 4,367,364 A | 1/1983 | Kulprathipanja et al. | 585/826 |
| 4,455,444 A | 6/1984 | Kulprathipanja et al. | 585/826 |
| 4,956,521 A | 9/1990 | Volles | 585/826 |
| 5,300,715 A | 4/1994 | Vora | 585/254 |

FOREIGN PATENT DOCUMENTS

WO  WO 99/07656  2/1999  ............. C07C/7/00

OTHER PUBLICATIONS

Schulz, R.C. (et al.) "LAB Production" Poster Session at the 2ⁿᵈ World Conference on Detergents Montreux, Switzerland Oct. 5–10, 1986.
Vora, B.V. (et al.) "Latest LAB Developments" *Hydrocarbon Processing* Nov. 1984 pp. 86–90.
Hoering, T.C. (et al.) "Shape-selective Sorption of Monomethylalkanes by Silicalite, a Zeolitic Form of Silica" *Journal of Chromatography* 316 (1984) pp. 333–341.

*Primary Examiner*—Thuan D. Dang
*Assistant Examiner*—Tam M. Nguyen
(74) *Attorney, Agent, or Firm*—John G. Tolomei; John F. Spears, Jr.

(57) ABSTRACT

Two separate paraffinic hydrocarbon products, such as normal and monomethyl branched $C_{10}$–$C_{23}$ paraffins, are recovered from a mixture comprising the product hydrocarbons and many other hydrocarbons in a process employing two adsorptive separation zones in series. A single desorbent comprising a light paraffin is used in both zones and recovered in a single system, thus reducing capital and operating costs. The recovered paraffinic hydrocarbons may then be dehydrogenated and reacted with benzene to form alkylaromatic hydrocarbons useful as a detergent precursor.

14 Claims, 1 Drawing Sheet

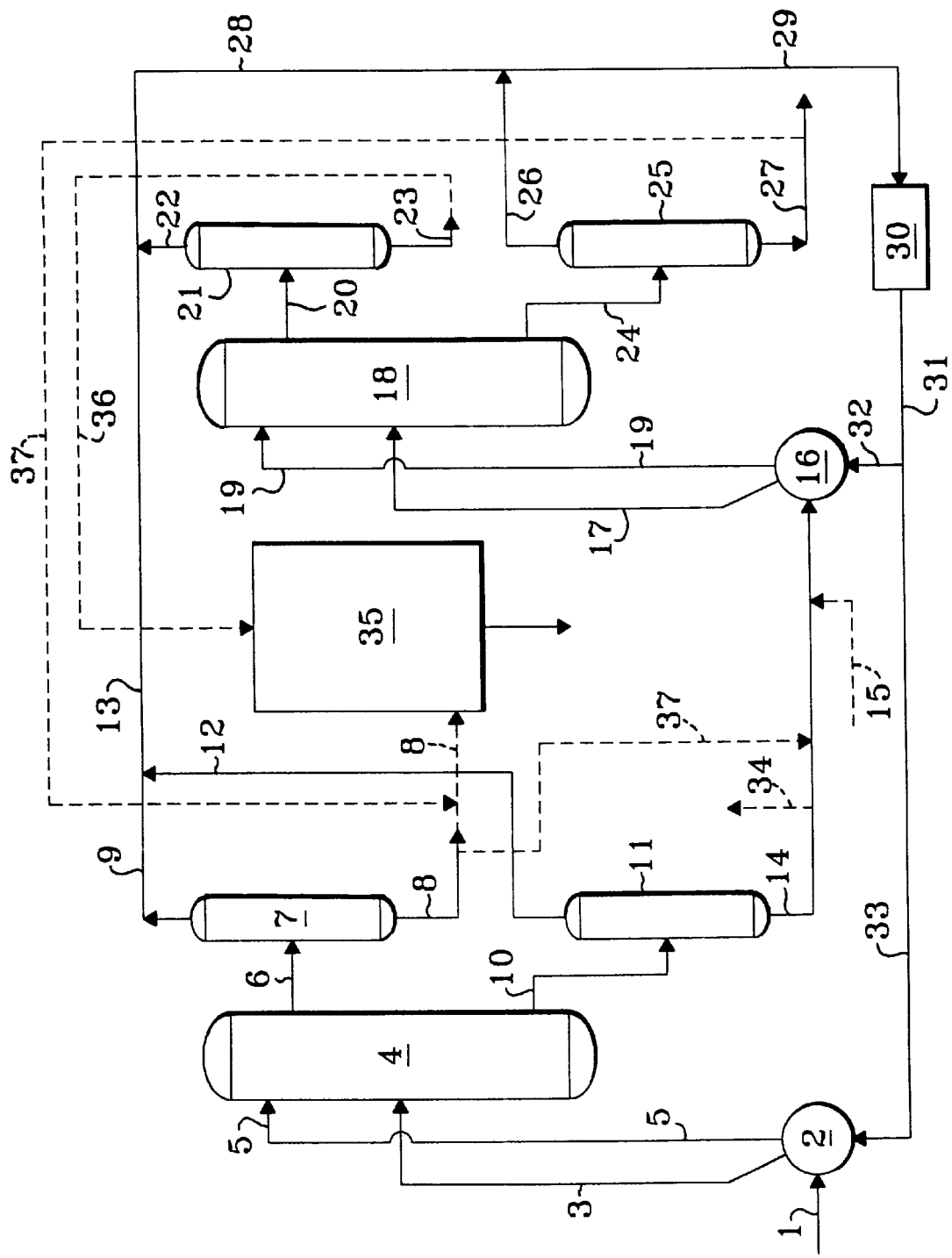

ADSORPTIVE SEPARATION PROCESS FOR RECOVERY OF TWO PARAFFIN PRODUCTS

BACKGROUND OF THE INVENTION

1. Field of the Invention

The invention relates to a process for the adsorptive separation of paraffinic hydrocarbons from a feed stream containing a broad admixture of hydrocarbons. More specifically the invention relates to a liquid-phase adsorptive separation process in which the feed stream flows through two different adsorptive separation zones in series and different paraffinic products are recovered from each separation zone.

2. Related Art

The large utility of detergents and other cleaners has led to extensive development in the areas of detergent formulation and production. While detergents can be formulated from a wide variety of different compounds much of the world's supply is now formulated from chemicals derived from linear alkyl benzenes (LAB). The LAB precursor compounds are produced in petrochemical complexes in which an aromatic hydrocarbon, typically benzene, is alkylated with olefin(s) of the desired structure and carbon number. Typically the olefin(s) is actually a homologous series of different olefins having a range of three to five carbon numbers. The olefin(s) can be derived from several sources. For instance, they can be derived from the oligomerization of $C_3$ or $C_4$ olefins or from the polymerization of ethylene. However, improved detergent characteristics led to the predominating use of straight chain (normal) olefins, and economics has led to the production of these olefins by the dehydrogenation of the corresponding paraffin. These paraffins, typically having 10 to 15 carbon atoms per molecule, are native to kerosene boiling range fraction of crude oils or processed fractions of crude oil. This led to the recovery of these naturally occurring desired paraffins from kerosene becoming the leading commercial source of olefins used in LAB production.

The production of the olefins typically starts with the recovery of paraffins of the appropriate carbon number by adsorptive separation from a hydrotreated kerosene boiling range fraction, which is the subject of this invention. The paraffins are then passed through a catalytic dehydrogenation zone wherein some of the paraffins are converted to olefins. The resultant mixture of paraffins and olefins is then passed into an alkylation zone in which the olefins are reacted with the aromatic substrate. This overall flow is shown in U.S. Pat. No. 2,477,382 issued to A. H. Lewis. A more complete description of this integrated process employing paraffin dehydrogenation and alkylation is shown in an article at page 86 of the November, 1984 edition of *Hydrocarbon Processing*.

A description of the use of simulated moving bed (SMB) adsorptive separation to recover paraffins from a kerosene boiling range petroleum fraction is provided in the contents of a presentation made by R. C. Schulz et al. at the 2nd World Conference on Detergents in Montreux, Switzerland on Oct. 5–10, 1986. This shows several incidental steps in the process such as fractionation and hydrotreating. A more detailed overall flow scheme for the production of olefins from the kerosene derived paraffins is presented in U.S. Pat. No. 5,300,715 issued to B. V. Vora.

The success of a particular adsorptive separation is determined by many factors. Predominant in these factors are the composition of the adsorbent (stationary phase) and desorbent (mobile phase) employed in the process. The remaining factors are basically related to process conditions. The subject process preferably employs two adsorbents with one being an adsorbent comprising a molecular sieve referred to in the art as silicalite. The use of silicalite in the adsorptive separation of paraffins is described in U.S. Pat No. 4,956,521 issued to W. K. Volles, which is directed to the production of high octane gasoline blending components. The sequential use of silicalite and zeolite 5A in the separation of monomethylalkanes is described in an article in the *Journal of Chromatography*, 316 (1984) 333–341. Silicalite has also been described as useful in separating normal paraffins from cyclic hydrocarbons and from branched chain hydrocarbons in U.S. Pat. Nos. 4,367,364 and 4,455,444 issued to S. Kulprathipanja and R. W. Neuzil. The separations described in these patents differs from that performed in the subject process as they correspond to that done in the previously cited article from the World Conference on Detergents, which is performed to recover only normal paraffins.

Several economic advantages are derived from the continuous, as compared to batch-wise, operation of a large scale adsorptive separation processes. Recognition of this has driven the development of simulated moving bed (SMB) adsorptive separation processes. These processes typically employ a rotary valve and a plurality of lines to simulate the countercurrent movement of an adsorbent bed through adsorption and desorption zones. This is depicted, for instance, in U.S. Pat. No. 3,205,166 to D. M. Ludlow, et al.

U.S. Pat. No. 3,510,423 to R. W. Neuzil et al. provides a depiction of the customary manner of handling the raffinate and extract streams removed from an SMB process, with the desorbent being recovered, combined and recycled to the adsorption zone. U.S. Pat. No. 4,006,197 to H. J. Bieser extends this teaching on desorbent recycling to three component desorbent mixtures. U.S. Pat. No. 4,036,745 describes the use of dual desorbents with a single adsorption zone to provide a higher purity paraffin extract.

More recent developments in the area of detergents have led to the discovery that alkylbenzene precursors derived from a mono-methyl paraffin can provide detergents having higher quality. This is described in PCT application WO 99/07656. This reference discloses (pages 7 and 23, FIG. 4) that two adsorptive separation zones may be used in series to produce streams of normal and monomethyl paraffins. Specifically, the feedstream to a second adsorption zone may be the raffinate of an upstream adsorptive separation zone. On page 28 this reference indicates the desorbents may include a lower molecular weight n-paraffin such as heptane or octane. This reference also describes the production of detergents and cleaning compounds from these materials.

BRIEF SUMMARY OF THE INVENTION

The invention is an adsorptive separation process for the recovery of normal acyclic paraffins in which the same desorbent is used in two different adsorptive separation zones recovering different products during the sequential flow of a single feed stream through the two zones. That is, the invention centers on the ability to use a single desorbent of the same composition in both adsorption zones, which reduces the complexity and costs of the overall process. The sequence of the two separation zones may be reversed to yield alternative process flows.

One broad embodiment of the invention may be characterized as an adsorptive separation process to recover both normal paraffins and monomethyl paraffins from a feed stream, which comprises passing a feed stream comprising normal and branched chain and cyclic paraffinic hydrocarbons having between 8 to 23 carbon atoms per molecule into a first adsorptive separation zone, which zone is maintained at adsorptive separation promoting conditions and which contains a first bed of selective adsorbent, selectively retaining a first class of paraffinic hydrocarbons in the first bed of selective adsorbent, and recovering from the first adsorptive separation zone a first raffinate stream comprising a desorbent and branched chain and cyclic paraffinic hydrocarbons which were not selectively retained on the first bed of selective adsorbent and a first extract stream comprising the desorbent and the first class of paraffinic hydrocarbons; passing paraffinic hydrocarbons recovered from either the first extract stream or the first raffinate stream into a second adsorptive separation zone, which second zone is maintained at adsorptive separation promoting conditions and which contains a second bed of selective adsorbent, selectively retaining a second class of paraffinic hydrocarbons on the selective adsorbent of the second bed, and recovering from the second adsorptive separation zone a second raffinate stream comprising the desorbent and paraffinic hydrocarbons which were not selectively retained on the first or second beds of selective adsorbent and a second extract stream comprising the desorbent and the second class of paraffinic hydrocarbons; fractionating the first and second extract streams and the first and second raffinate streams to recover desorbent and producing first and second extract product streams; and passing portions of the thus recovered desorbent into both the first and the second adsorptive separation zones for use in desorbing paraffinic hydrocarbons to produce the first and second extract streams.

A more specific embodiment of the invention is an adsorptive separation process which comprises passing a feed stream comprising alicyclic hydrocarbons, and normal and branched paraffinic hydrocarbons having between 8 to 15 carbon atoms per molecule into a first adsorptive separation zone, which zone is maintained at adsorptive separation promoting conditions and which contains a first bed of selective adsorbent, selectively retaining a first paraffinic hydrocarbon on at least a portion of the first bed selective adsorbent, and recovering from the first adsorptive separation zone a first raffinate stream comprising a desorbent and paraffinic hydrocarbons which were not selectively retained on the first bed of selective adsorbent; passing paraffinic hydrocarbons present in the first raffinate stream into a second adsorptive separation zone, which second zone is maintained at adsorptive separation promoting conditions and which contains a second bed of selective adsorbent, selectively retaining a second paraffinic hydrocarbon on at least a portion of the second bed selective adsorbent, and recovering from the second adsorptive separation zone a second raffinate stream comprising the desorbent and paraffinic hydrocarbons which were not selectively retained on the first or second beds of selective adsorbent; passing a first desorbent stream, comprising the desorbent, into the first adsorptive separation zone and desorbing paraffinic hydrocarbons to produce a first extract stream comprising the first paraffinic hydrocarbon and the desorbent; passing a second desorbent stream, comprising the desorbent, into the second adsorptive separation zone and desorbing paraffinic hydrocarbons to produce a second extract stream comprising the second paraffinic hydrocarbon and the desorbent; fractionating the first and second extract streams to recover the desorbent for reuse in the process.

BRIEF DESCRIPTION OF THE DRAWING

The drawing is a simplified flow diagram of a process unit for the recovery of two different paraffinic products by use of simulated moving bed adsorptive separation in two sequential separation zones employing the same desorbent.

DETAILED DESCRIPTION AND PREFERRED EMBODIMENTS

Natural soaps are sodium salts of fatty acids which are obtained by alkaline saponification of triglycerides from vegetable or animal sources. Natural soaps of this nature were prevalent until the 1940's when sodium alkyl benzene sulfonates became available. These synthetic soaps had superior detergency characteristics compared to natural soaps and lower cost, and the new surfactants displaced natural soaps in household laundry and dishwashing applications.

The first alkylbenzene sulfonates were obtained by the Friedel-Crafts alkylation of benzene with propylene tetramer. The tetramer is a mixture of highly branched $C_{12}$ olefins, and the alkylbenzene sulfonate made by sulfonation of the dodecylbenzenes with oleum or sulfur trioxide followed by neutralization with sodium hydroxide is also highly branched. The dodecylbenzene sulfonate is an effective detergent but it has a very slow rate of biodegradation. In the 1960's linear alkylbenzene sulfonates (LABS) were introduced as a biodegradable replacement.

The linear olefins required for the production of linear alkyl benzene (LAB) used in LABS production is now made mainly by the route outlined above. That is, straight chain paraffins are adsorbed from a purified petroleum fraction and then dehydrogenated. As mentioned above, and in great detail in U.S. Pat. No. 6,020,303, it appears that surfactants derived from certain paraffins having limited mid-chain branching may have superior overall properties to those from straight chain paraffins. This overall superiority is based upon such factors as cold water sudsing and performance in hard water, in addition to biodegradability and detergency. A mixture of these mid-chain branched paraffins with normal paraffins may also be more highly desired as the precursor paraffin used in the production of LAB. The slightly branched mid-chain paraffins believed to be most useful in LAB production are monomethyl paraffins, a term used herein to refer to acyclic paraffins having a methyl branch extending from the primary carbon chain used for nomenclature. Preferably, the monomethyl paraffins do not have side chain branches containing more than two carbon atoms. Most preferably, the monomethyl paraffins have only a single methyl branch.

It is an objective of this invention to provide an improved adsorptive separation process which may be used to produce paraffins used in the manufacture of LAB. It is a further objective of the subject process to provide a simulated moving bed adsorptive separation process which produces two separate paraffin product streams. It is a specific objective of the invention to provide a simulated moving bed adsorptive separation process which recovers separate product streams comprising normal paraffins and monomethyl paraffins from a single mixed hydrocarbon feed stream at reduced cost.

The subject invention achieves these objectives by the use of a unique flow scheme that requires the use of only one desorbent, thereby reducing the size and complexity of the required desorbent recovery system. The invention can in some instances also reduce the complexity of the product recovery fractionation system.

In the practice of the present invention, a feed mixture comprising two or more classes of hydrocarbons such as paraffins of different skeletal structure and also other different hydrocarbons is passed through one or more beds of an adsorbent which selectively adsorbs desired paraffins of one class (skeletal structure) or both classes while permitting other components of the feed stream to pass through the adsorption zone in an unchanged condition and become part of a raffinate stream. The flow of the feed through the adsorbent bed is stopped and the adsorption zone is then flushed to remove nonadsorbed materials surrounding the adsorbent. Thereafter the adsorbed paraffin is desorbed from the adsorbent by passing a desorbent stream through the adsorbent bed as an extract stream. The desorbent material is commonly also used to flush nonadsorbed materials from the void spaces around and within the adsorbent. Hydrocarbons from one of the two effluents of this first adsorption step are then passed into a second adsorption zone similar to the first. The same desorbent is used in the second zone to generate another extract stream, and the desorbent recovered from the extract and raffinate streams of both adsorption steps is recycled.

The adsorption and desorption steps can be performed in a single large bed of adsorbent or in several parallel beds on a swing bed basis. However, it has been found that simulated moving bed adsorptive separation provides several advantages such as high purity and recovery. Therefore, many commercial scale petrochemical separations, especially those for the separation of mixed paraffins are performed using simulated countercurrent moving bed (SMB) technology. The previously sited references are incorporated for their teaching on the performance of this technique. Further details on equipment and techniques for using in an SMB process may be found in U.S. Pat. Nos. 3,208,833; 3,214,247; 3,392,113; 3,455,815; 3,523,762; 3,617,504; 4,006,197; 4,133,842; and 4,434,051. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991.

The overall process flow of the subject invention can be best described by reference to the Drawing. The Drawing is a simplified flow diagram depicting preferred and alternative embodiments of the invention. A feed stream comprising a mixture of $C_9$–$C_{14}$ hydrocarbons including normal paraffins, monomethyl isoparaffins and more highly branched isoparaffins is passed into the process via line 1. The feed may also contain a wide variety of structural types of co-boiling hydrocarbons including naphthenes and aromatics. It is preferred that the feed stream contains essentially only $C_9$–$C_{14}$ hydrocarbons and is produced by fractionating hydrocarbons derived from kerosene. The feed stream enters a first rotary valve 2 which is employed to direct the flow of the feed, desorbent, extract and raffinate streams of the process through a plurality of bed lines, not shown, which extend from the rotary valve to the adsorbent chamber 4. A commercial SMB process unit may have from 8 to 24 or more such bed lines between the valve and a corresponding number of adsorbent beds in one or two adsorbent chambers. This plurality of lines is used in the performance of the simulated moving bed separation process, which is the preferred mode of operation of the adsorption zone. However, only bed line 3, which at the time depicted is being used to carry the feed stream from the rotary valve to the adsorbent chamber 4, and desorbent bed line 5 are shown on the drawing. This depiction therefore only shows the feed and desorbent stream bed line flows at one particular point in time. Other bed lines are used as the locations of the adsorption zone and desorption zones are gradually shifted within the adsorbent chamber 4. The feed stream enters the adsorbent chamber and passes downward through a fixed mass of an adsorbent which selectively retains a hydrocarbon or class of hydrocarbon. This mass of adsorbent normally is formed from several sub-beds, each having a separate inlet line, not shown.

In the embodiment being described the adsorbent selectively retains normal paraffins as a class. The remainder of the feed stream e.g. branched paraffins including monomethyl paraffins passes through the adsorption zone and is removed from the adsorbent chamber 4 as part of a raffinate stream of line 10. The raffinate stream of line 10 will also contain desorbent hydrocarbons which were originally present in the adsorption zone 4. The raffinate stream therefore comprises both unadsorbed feed and desorbent compounds. It is passed into a fractionation column 11, often referred to as the raffinate column. The components of the raffinate stream are separated therein, with the more volatile desorbent compounds being concentrated into a net overhead stream removed in line 12 and the remaining (unadsorbed) components of the feed stream being a removed as the bottoms stream of line 14. For purposes of simplicity the raffinate stream is shown as passing directly into the raffinate column. In an SMB process this stream actually flows into the rotary valve 2 through one of the many unshown bed lines and is then directed to the raffinate column. All of the effluent streams removed from the two adsorbent chambers 4 and 18 employed in the process have similar flows which pass through the rotary valve as described herein. Alternate means of interconnecting the numerous sub-beds of the adsorption zones to the columns, such as a grid or manifold of valves, may be employed if desired.

In the preferred embodiment of the invention the raffinate materials of line 14 are passed into an adsorbent chamber 18 of a second simulated moving bed adsorptive separation zone via a second rotary valve 16. However, in an alternative embodiment of the invention a portion of raffinate material of line 14 is removed from the process as a product stream carried by optional line 34. The hydrocarbons of line 34 are a valuable product in their own right which can be sold if not totally consumed in the process. A dashed line is also used to indicate the possible optional flow of a second external feed stream into the process via line 15. This stream should comprise the desired extract component(s) of the second adsorption step. It may differ in composition from the raffinate product stream of line 14.

The arrangement of equipment and operation in the second separation zone is similar to that in that in the first. The hydrocarbons of line 14 are directed into a bed line 17 by the rotary valve. These are the raffinate hydrocarbons of line 14 and contain substantially all of the non-normal hydrocarbons of the original feed stream of line 1 including the monomethyl paraffins. This second feed stream flows into the adsorbent chamber 18 of the second adsorption zone and downward through the adsorption zone of chamber 18 contacting a mass of a different second adsorbent, which is selective for a different structural class of hydrocarbon than the adsorbent used in the first adsorbent chamber 4. In the preferred embodiment of the invention the hydrocarbons preferentially retained in the second zone are monomethyl branched paraffins. The remaining hydrocarbons flow from the adsorbent chamber 18 in a second raffinate stream carried by line 24. This second raffinate stream will also contain desorbent displaced from the adsorptive zone and is therefore passed via line 24 into a second raffinate column 25 for desorbent recovery. As before, this stream would actually flow through the rotary valve 16 via a bed line not shown. In raffinate column 25 the entering hydrocarbons are separated by fractional distillation into a net overhead stream rich in desorbent compounds, carried by line 26, and a net bottoms stream carried by line 27 containing the unadsorbed, raffinate compounds such as naphthenes, highly branched paraffins and aromatics. This stream is discharged from this process.

The hydrocarbons which are selectively adsorbed on the adsorbents in the two adsorbent chambers are removed by passing a stream of desorbent through the adsorbent. In the case of adsorption chamber 4 the first rotary valve 2 distributes a recycle desorbent stream from line 33 into the appropriate bed line including line 5. At the point in time depicted, line 5 carries the desorbent stream to a position in the adsorbent chamber which marks the beginning of the desorption zone. This zone comprises a second mass of adsorbent located in chamber 4. The desorbent stream flows downward through the adsorption zone pushing out hydrocarbons in the void volume around adsorbent particles and also dislodging the selectively adsorbed feed component(s) from the first adsorbent. The combined flow of desorbent compound, void volume compounds and released extract compounds is removed from the adsorption chamber 4 via line 6 as a first extract stream and passed into a fractional distillation column 7 referred to as an extract column. Again the flow depicted on the drawing has been simplified by excluding the flow through the rotary valve 2. The conditions imposed within the first extract column lead to the separation of the entering compounds into a net overhead stream, rich in the desorbent compounds, carried by line 9 and a net bottoms stream, comprising the extract normal paraffins carried by line 8. The net bottoms stream is removed from the process as a first extract product stream. The extract product may be passed to an external dehydrogenation zone to produce olefins for LAB manufacture or into an LAB production zone 35 containing both dehydrogenation and alkylation zones.

At the second rotary valve 16 a second stream of desorbent carried by line 32 is distributed to a bed line 19 in a manner similar to that of the first adsorption zone. The desorbent then flows into the adsorption chamber 18 and downward through a mass of the second adsorbent forming the desorption zone of this chamber. This removes the second class of selectively adsorbed paraffins, the monomethyl paraffins, and forms a second extract stream comprising an admixture of desorbent and extract paraffins. This second extract stream is withdrawn via line 20 and passed into the second extract column 21 via a connection with the rotary valve not shown. The second extract stream is separated in column 21 to yield a stream of desorbent carried by line 22 and a second extract product stream carried by line 23. The second extract stream may be withdrawn from the process as a product or this stream may be passed to the same or a different dehydrogenation zone as the first extract stream. In yet another alternative embodiment of the invention the second extract stream is passed via line 23 into the LAB production zone 35.

The desorbent streams of lines 9 and 12 are combined to form the desorbent stream of line 13. The desorbent flowing through line 22 is combined with this steam and passed into line 28. The desorbent of line 26 is finally mixed into this flow to form the desorbent stream of line 29 which is recycled to the adsorption zones via lines 33 and 31. An optional treating and surge dampening zone 30 is shown as being located in the line carrying the total desorbent flow.

The degree of integration of the desorbent collection, storage and handling systems is a matter of some variation depending on the desired operational freedom of the process. Theoretically all of the overhead systems of the four columns 7, 11, 21, and 25 could be combined as they should all be high purity streams of desorbent. This would allow for the utilization of a single overhead condenser and receiver which would presumably reduce capital costs. However, this high degree of integration may lead to other problems such as more complicated startup procedures, an increased chance of contamination during upsets and fewer degrees of operational freedom due to interoperability requirements of the integrated process. For this reason, the preferred flow as shown in the Drawing simply collects desorbent from the overhead of each of the four columns into a central handling system.

The adsorbent chambers of the first and second adsorption zones can be operated at similar temperature and pressure conditions as described in detail below. The temperature or other operating variables may also differ between the two zones. The difference in their separation capability is primarily due to the use of different adsorbents. The first adsorption zone preferably uses an adsorbent based upon a 5A molecular sieve. The second adsorption zone preferably uses an adsorbent based upon a molecular sieve referred to as silicalite described in detail below.

A preferred embodiment of the subject invention can accordingly be characterized as an adsorptive separation process which comprises passing a feed stream comprising aromatic hydrocarbons, naphthenes, and co-boiling normal and branched paraffinic hydrocarbons having from 8 to 15 carbon atoms per molecule into a first adsorptive separation zone, which zone contains a first bed of selective adsorbent maintained at adsorptive separation promoting conditions, selectively retaining a normal first paraffinic hydrocarbon on at least a portion of the first bed of selective adsorbent, and recovering from the first adsorptive separation zone a first raffinate stream comprising a desorbent and paraffinic hydrocarbons which were not retained on the first bed of selective adsorbent; fractionating the first raffinate stream to remove desorbent and produce a raffinate product stream, and passing at least a portion of the raffinate product stream into a second adsorptive separation zone, which second zone contains a bed of a second selective adsorbent maintained at adsorptive separation promoting conditions, selectively retaining a monomethyl second paraffinic hydrocarbon on at least a portion of the selective adsorbent, and recovering from the second adsorptive separation zone a second raffinate stream comprising the desorbent and paraffinic hydrocarbons which were not selectively retained on the first bed or second bed of selective adsorbent; passing a first desorbent stream, comprising the desorbent, through the first adsorptive separation zone and desorbing paraffinic hydrocarbons to produce a first extract stream a comprising the normal first paraffinic hydrocarbon and the desorbent; passing a second desorbent stream, comprising the desorbent, through the second adsorptive separation zone and desorbing paraffinic hydrocarbons to produce a second extract stream comprising the monomethyl second paraffinic hydrocarbon and the desorbent; and fractionating the first and second extract streams to recover the desorbent for reuse in the process.

As mentioned above, the flows in the subject invention are subject to considerable variation. The major driver of this variation is economics which in turn is governed by product prices and technology. Both of these latter factors change. One very fundamental variable in the subject process is the order in which the two selective adsorbents are employed. In the preferred embodiment described above the first adsorptive separation zone employed an adsorbent comprising 5A sieve and produced an extract containing normal paraffins. The monomethyl paraffins remain in the raffinate and the recovered raffinate hydrocarbons are passed into the second adsorptive separation zone. In a totally different processing sequence, the first adsorptive separation zone is loaded with a silicalite based adsorbent and both the monomethyl paraffins and the normal paraffins are selectively retained. These two structural classes are then both removed from the adsorbent by the desorbent and become part of the extract. The extract product, therefore, contains both the normal paraffins and the monomethyl paraffins and they are passed into the second adsorptive separation zone. This is shown in the Drawing by the bottoms of extract column 7 being passed into optional line 37 which carries it to line 14. Line 14 in turn carries the extract product stream to the second rotary valve 16. The final result of this is that the normal paraffins are retained in the adsorbent chamber 18 and eventually removed by the desorbent to form the extract stream of line 20. After desorbent recovery all or a portion of the normal paraffins can be passed to the dehydrogenation and alkylation zone 35 via optional line 36. The monomethyl paraffins are removed in the raffinate stream of line 24 and discharged as a product via line 27. All or a portion of the monomethyl paraffins can be passed into the dehydrogenation and alkylation zone 35 via optional line 37.

This alternative flow arrangement results in the feed stream to the second adsorptive separation zone being much smaller, therefore reducing the size and cost of the adsorbent chamber, rotary valve, columns, etc. However, due to the silicalite sieves having a lower capacity in this service, the second adsorptive separation chamber will increase in size. The relative concentration of these two classes of paraffins in the feed stream of line 1 will also be a factor. Therefore, preferences are determined by a technology factors such as adsorbent capability and economic factors such as the desired product ratio of normal to monomethyl paraffins.

Feed mixtures which can be utilized in the process of this invention will typically be prepared by either prior separation step(s) or by relatively specific oligomerization reactions. Such feed preparation methods are inherently imprecise and produce a stream containing a mixture of compounds. Thus, the feed mixtures to the process of this invention can contain a wide variety of co-boiling hydrocarbons and may contain paraffins having multiple branches and paraffins having multiple carbon atoms in the branches, cycloparaffins, branched cycloparaffins or other compounds having boiling points relatively close to the desired extract paraffins. It is expected that separation methods recovering paraffins from hydrotreated petroleum fractions will provide the lowest cost feed and will therefore be the predominate feed source. The carbon number range of the normal and monomethyl paraffins desired for the production of LAB is normally between about 9 and about 16, with 10 to 14 or 9 to 13 often being preferred. This range corresponds to linear paraffins boiling in the kerosene boiling point range, and kerosene fractions produced in petroleum refineries either by crude oil fractionation or by conversion processes form suitable feed precursors. The boiling point range of the feed may extend upward to cover heavier hydrocarbons having a carbon number of 23 or more such that the feed may be a $C_8$–$C_{23}$ fraction. Fractions recovered from crude oil by fractionation will typically require hydrotreating for removal of sulfur and/or nitrogen prior to being fed to the subject process. The boiling point range of the kerosene fraction can be adjusted by prefractionation to adjust the carbon number range of the paraffins. In an extreme case the boiling point range can be limited such that only paraffins of a single carbon number predominate. Kerosene fractions also contain a very large number of different hydrocarbons and the feed to the subject process can therefore contain 200 or more different paraffinic hydrocarbons.

The paraffin streams recovered from the two adsorption zones of the process can be processed independently via dehydrogenation and aromatic alkylation to produce two separate alkylbenzene products. As an alternative, only portions of each stream could be used to form a desired paraffin blend, or olefins derived from each paraffin could be admixed prior to alkylation. For instance, all of the normal paraffins recovered in the first adsorption zone could be mixed with one-half of the monomethyl paraffins recoverable in the second zone and the resultant admixture passed into a single dehydrogenation zone to form olefins consumed in alkylbenzene production. The second adsorption zone can then be significantly smaller in capacity and cost than if all the potential second stage product is recovered. This can be achieved by changed operating conditions or a reduced feed rate and zone size. This "ratioing" of the amounts of normal and monomethyl paraffins which are blended to form the dehydrogenation zone feed will be largely set by the desired composition of the alkylbenzene blend produced by the alkylation zone. The operating or separation promoting conditions in the two zones may be adjusted to some extent to control the purity and the flow rate of the extract paraffin products and to control the relative percentage of recovery in each adsorption zone. This allows some adjustment in the ratio of normal to monomethyl paraffin produced in the process. It is expected that normally all of both paraffinic products would be used for alkylbenzene production. This is represented on the drawing by passage of the second extract stream into the alkylbenzene production zone 35 via optional line 36.

The two classes of product paraffinic hydrocarbons may be passed as separate streams or as a single stream into a dehydrogenation or carbonylation zone or a combined dehydrogenation and alkylation process to convert the paraffinic hydrocarbons into detergent precursors. These conversion zones may be of conventional design. The previously cited references are incorporated by reference for their teaching as to the production of linear alkyl benzene (LAB) as detergent precursors. The conversion of these precursors to actual detergents is also performed by conventional means. It is also possible to produce a number of different detergent precursors through carbonylation or dehydrogenation alone without resorting to alkylation. These are based primarily on linear structures such as alpha-olefin sulfonates (AOS), secondary alkane sulfonates (SAS), linear alcohol ethoxylate nonionics (NI) and linear alcohol ethoxy sulfates (AES). The latter two materials are made, respectively, by reacting a linear alcohol, either primary or secondary, with about 7 to 10 moles of ethylene oxide and by the sulfation of low molecular weight ethyoxylates of linear alcohols (3 to 4 moles of ethylene oxide) as with sulfur trioxide or chlorosulfonic acid. Both sodium and ammonium salts of these compounds are useful as surfactants.

Operating conditions for both adsorption chambers 4 and 18 include, in general, a temperature range of from about 20 to about 250° C., with from about 60 to about 200° C. being preferred. Different operating conditions may be preferred in the two adsorption zones. Lower temperatures from 75° C. to 160° C. are highly preferred for the second adsorption zone when recovering monomethyl paraffins in this zone. There is a tradeoff between higher recovery at higher temperatures and higher purity at lower temperatures. Adsorption promoting conditions also include a pressure sufficient to maintain the process fluids in liquid phase; which may be from about atmospheric to 600 psig. Desorption conditions generally include the same temperatures and pressure as used for adsorption conditions. It is generally preferred that an SMB process is operated with an A:F flow rate through the adsorption zone in the broad range of about 1:1 to 5:0.5 where A is the volume rate of "circulation" of selective pore volume and F is the feed flow rate. The practice of the subject invention requires no significant variation in operating conditions, adsorbent or desorbent composition within the adsorbent chambers. That is, the adsorbent in a chamber preferably remains at the same temperature throughout the process.

The adsorbent used in the first adsorption zone preferably comprises silicaalumina molecular sieves having relatively uniform pore diameters of about 5 angstroms. This is provided by commercially available type 5A molecular sieves produced by the adsorbents group of UOP LLC, formerly the Linde Division of Union Carbide Corporation.

The preferred adsorbent for the second adsorption zone comprises silicalite. Silicalite is well described in the literature. For instance, it is disclosed and claimed in U.S. Pat. No. 4,061,724 issued to Grose et al. A more detailed description is found in the article, "Silicalite, A New Hydrophobic Crystalline Silica Molecular Sieve," *Nature, Vol.* 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å circular and 5.1–5.7 Å elliptical on the major axis. This gives silicalite great selectivity as a size selective molecular sieve. Due to its essentially aluminum free e.g., silica to alumina ratio of 300 or higher, structure composed of silicon dioxide, silicalite does not show ion-exchange behavior. Thus silicalite is not a zeolite. Silicalite is also described in U.S. Pat. Nos. 5,262,144; 5,276,246 and 5,292,900. These patents basically relate to treatments which reduce the catalytic activity of silicalite to allow its use as an adsorbent.

The active component of the adsorbents is normally used in the form of particulate agglomerates having higher physical strength and attrition resistance than the active components themselves. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica as appropriate are generally used as binders.

The active molecular sieve component of the adsorbents will ordinarily be in the form of small crystals present in the adsorbent particles in amounts ranging from about 75 to about 98-wt.% of the particle based on volatile-free composition. Volatile-free compositions are generally determined after the adsorbent has been calcined at 900° C. in order to drive off all volatile matter. The remainder of the adsorbent will normally be the inorganic matrix of the binder present in intimate mixture with the small particles of the adsorbent material. This matrix material may be an adjunct of the manufacturing process for the silicalite, for example, from the intentionally incomplete purification of the silicalite during its manufacture.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the range of from 0 to 4.0 wt.%. As is well known in the art, the hydration level of the sieve is maintained by control of the water concentration in the feed and desorbent streams.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component, and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which insures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

The preferred desorbent of the subject process comprises a mixture of a normal paraffin and an isoparaffin or cycloparaffin (naphthene). A mixture in which the normal and cycloparaffins have the same carbon number is highly preferred, with carbon numbers of the desorbent compounds being in the general range of 5 to 8. Preferred cycloparaffins are cyclopentane, cyclohexane and methyl cyclohexane. A preferred iso-paraffin is isooctane. The preferred normal paraffins are n-hexane or n-pentane, and the desorbent may range from 0 to 100% normal paraffin. N-hexane is actually the strongest desorbent of these compounds, and a blend of normal and cyclo paraffins is often desired to adjust the strength of the desorbent. These blends may contain from about 10 to 90 vol. percent cycloparaffin, with the remainder being the normal paraffin. A desorbent blend containing 40 to 60 percent cycloparaffin is preferred. The desorbent may also be 100% cycloparaffin.

U.S. Pat. No. 4,992,618 issued to S. Kulprathipanja describes the use of a "prepulse" of a desorbent component in an SMB process recovering normal paraffins. The prepulse is intended to improve the recovery of the extract normal paraffins across the carbon number range of the feed. The prepulse enters the adsorbent chamber at a point before (downstream) of the feed injection point. A different SMB processing technique is the use of "zone flush." The zone flush forms a buffer zone between the feed and extract bed lines to keep the desorbent e.g. normal pentane, from entering the adsorption zone. While the use of a zone flush requires a more complicated, and thus more costly rotary valve, the use of zone flush is preferred in the adsorption zones when high extract recovery is desired. In practice, a quantity of a mixed component desorbent recovered overhead from the extract and/or raffinate columns is passed into a separate splitter column. A high purity stream of the lower strength component of the mixed component desorbent is recovered and used as the zone flush stream. Further information on the use of dual component desorbents and on techniques to improve product purity such as the use of flush streams may be obtained from U.S. Pat. Nos. 3,201,491; 3,274,099; 3,715,409; 4,006,197 and 4,036,745 which are incorporated herein by reference for their teaching on these aspects of SMB technology.

For purposes of this invention, various terms used herein are defined as follows. A "feed mixture" is a mixture containing one or more extract components and one or more raffinate components to be separated by the process. The term "feed stream" indicates a stream of a feed mixture which is passed into contact with the adsorbent used in the process. An "extract component" is a compound or class of compounds that is more selectively adsorbed by the adsorbent while a "raffinate component" is a compound or type of compound that is less selectively adsorbed. The term "desorbent material" shall mean generally a material capable of desorbing an extract component from the adsorbent. The term "raffinate stream" or "raffinate output stream" means a stream in which a raffinate component is removed from the adsorbent bed after the adsorption of extract compounds. The composition of the raffinate stream can vary from essentially 100% desorbent material to essentially 100% raffinate components. The term "extract stream" or "extract output stream" means a stream in which an extract material, which has been desorbed by a desorbent material, is removed from the adsorbent bed. The composition of the extract stream can vary from essentially 100% desorbent material to essentially 100% extract components.

At least portions of the extract stream and the raffinate stream are passed to separation means, typically fractional distillation columns, where at least a portion of desorbent material is recovered and an extract product and a raffinate product are produced. The terms "extract product" and "raffinate product" mean streams produced by the process containing, respectively, an extract component and a raffinate component in higher concentrations than those found in the extract stream and the raffinate stream withdrawn from adsorbent chamber. The extract stream may be rich in the desired compound or may only contain an increased concentration. The term "rich" is intended to indicate a concentration of the indicated compound or class of compounds greater than 50 mole percent.

It has become customary in the art to group the numerous beds in the SMB adsorption chamber(s) into a number of zones. Usually the process is described in terms of 4 or 5 zones. First contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired isomer and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563. The terms "upstream" and "downstream" are used herein in their normal sense and are interpreted based upon the overall direction in which liquid is flowing in the adsorbent chamber. That is, if liquid is generally flowing downward through a vertical adsorbent chamber, then upstream is equivalent to an upward or higher location in the chamber.

What is claimed:

1. An adsorptive separation process to recover both normal paraffins and monomethyl paraffins from a feed stream, which process comprises:
   (a) passing a feed stream comprising normal and branched chain and cyclic paraffinic hydrocarbons having from 8 to 23 carbon atoms per molecule into a first adsorptive separation zone, which zone is maintained at adsorptive separation promoting conditions and which contains a first bed of selective adsorbent, selectively retaining a first class of paraffinic hydrocarbons in the first bed of selective adsorbent, and recovering from the first adsorptive separation zone a first raffinate stream comprising a desorbent and branched chain and cyclic paraffinic hydrocarbons which were not selectively retained on the first bed selective adsorbent and a first extract stream comprising the desorbent and the first class of paraffinic hydrocarbons;

(b) passing parrafinic hydrocarbons recovered from either the first extract stream or the first raffinate stream into a second adsorptive separation zone, which second zone is maintained at adsorptive separation promoting conditions and which contains a second bed of selective adsorbent, selectively retaining a second class of paraffinic hydrocarbons on the selective adsorbent of the second bed, and recovering from the second adsorptive separation zone a second raffinate stream comprising the desorbent and parrafinic hydrocarbons which were not selectively retained on the first or second beds of selective adsorbent and a second extract stream comprising the desorbent and the second class of paraffinic hydrocarbons;

(c) fractionating the first and second extract streams and the first and second raffinate streams to recover desorbent from the first and second adsorptive separation zones, and producing first and second extract product streams; and (d) admixing desorbent recovered from the first and second adsorptive separation zones to form a recovered desorbent stream, and passing a portion of the recovered desorbent stream into both the first and the second adsorptive separation zones for use in desorbing paraffinic hydrocarbons to produce the first and second extract streams.

2. The process of claim 1 wherein normal and monomethyl paraffins are present in the first extract stream and are passed into the second adsorptive separation zone.

3. The process of claim 1 wherein monomethyl and cyclic paraffins are present in the first raffinate stream and are passed into the second adsorptive separation zone.

4. An adsorptive separation process which comprises:
(a) passing a feed stream comprising alicyclic hydrocarbons, and normal and branched paraffinic hydrocarbons having between 8 to 15 carbon atoms per molecule into a first adsorptive separation zone, which zone is maintained at adsorptive separation promoting conditions and which contains a first bed of selective adsorbent, selectively retaining a first paraffinic hydrocarbon on at least a portion of the first bed of selective adsorbent, and recovering from the first adsorptive separation zone a first raffinate stream comprising a desorbent and paraffinic hydrocarbons which were not selectively retained on the first bed of selective adsorbent;

(b) passing paraffinic hydrocarbons present in the first raffinate stream into a second adsorptive separation zone, which second zone is maintained at adsorptive promoting separation conditions and which contains a second bed of selective adsorbent, selectively retaining a second paraffinic hydrocarbon on at least a portion of the second bed of selective adsorbent, and recovering from the second adsorptive separation zone a second raffinate stream comprising the desorbent paraffinic hydrocarbons which were not selectively retained on the first or second beds of selective adsorbent;

(c) passing a first desorbent stream, comprising the desorbent, into the first adsorptive separation zone and desorbing paraffinic hydrocarbons to produce a first extract stream comprising the first paraffinic hydrocarbon and the desorbent;

(d) passing a second desorbent stream, comprising the desorbent, into the second adsorptive separation zone and desorbing paraffinic hydrocarbons to produce a second extract stream comprising the second paraffinic hydrocarbon and the desorbent;

(e) combining desorbent recovered by fractionating the first and second extract streams for reuse in the process.

5. The process of claim 4 further characterized in that the first and second extract streams are fractionated in different fractionation columns and separate overhead streams comprising the desorbent compound are obtained from the fractionation columns, combined and then recycled within the process.

6. The process of claim 4 further characterized in that the first and the second raffinate streams are passed into separate fractionation columns and separated therein into separate raffinate product streams.

7. The process of claim 6 further characterized in that a third and a fourth desorbent streams are produced by fractionation of the first and second raffinate streams and combined and recycled within the process.

8. The process of claim 4 further characterized in that desorbent recovered during the fractionation of the first and second extract streams and desorbent recovered by the fractionation of the first and second raffinate streams is combined, and the resultant combined desorbent is employed in the process to provide desorbent to the two adsorption zones.

9. The process of claim 4 further characterized in that the first and the second desorbent streams comprise a mixture of an isoparaffin and a normal paraffin.

10. An adsorptive separation process which comprises:
(a) passing a feed stream comprising aromatic hydrocarbons, naphthenes, and co-boiling normal and branched paraffinic hydrocarbons having from 8 to 15 carbon atoms per molecule into a first adsorptive separation zone, which first separation zone contains a first bed of selective adsorbent maintained at adsorptive separation promoting conditions, selectively retaining a normal first paraffinic hydrocarbon on at least a portion of the first bed of selective adsorbent, and recovering from the first adsorptive separation zone a first raffinate stream comprising a desorbent and paraffinic hydrocarbons which were not retained on the first bed of selective adsorbent;

(b) fractionating the first raffinate stream to remove desorbent and produce a raffinate product stream, and passing at least a portion of the raffinate product stream into a second adsorptive separation zone, which second separation zone contains a bed of a second selective adsorbent maintained at adsorptive separation promoting conditions, selectively retaining a monomethyl second paraffinic hydrocarbon on at least a portion of the selective adsorbent, and recovering from the second adsorptive separation zone and a second raffinate stream comprising the desorbent and paraffinic hydrocarbons which were not selectively retained on the first bed or second bed of selective adsorbent;

(c) passing a first desorbent stream, comprising the desorbent, through the first adsorptive separation zone and desorbing paraffinic hydrocarbons to produce a first extract stream comprising the normal first paraffinic hydrocarbon and the desorbent;

(d) passing a second desorbent stream, comprising the desorbent, through the second adsorptive separation zone and desorbing paraffinic hydrocarbons to produce a second extract stream comprising the second paraffinic hydrocarbon and the desorbent; and (e) combining desorbent recovered by fractionating the first and second extract streams for reuse in the process.

11. The process of claim 10 further characterized in that the first paraffinic hydrocarbon is a normal paraffin having the same number of carbon atoms per molecule as the second paraffinic hydrocarbon.

12. The process of claim 11 further comprising passing the first and the second paraffinic hydrocarbons into a dehydrogenation zone and producing olefinic hydrocarbons.

13. The process of claim 12 further comprising converting the olefinic hydrocarbons into a detergent.

14. An adsorptive separation process which comprises:

(a) passing a feed stream comprising naphthenes and normal and branched paraffinic hydrocarbons having from 8 to 15 carbon atoms per molecule into a first adsorptive separation zone, which zone contains a first bed of selective adsorbent maintained at adsorptive separation promoting conditions, selectively retaining normal and monomethyl branched paraffinic hydrocarbons on at least a portion of the first bed of selective adsorbent, and recovering from the first adsorptive separation zone a first raffinate stream comprising naphthenes and paraffinic hydrocarbons which were not retained on the first bed of selective adsorbent;

(b) passing a first desorbent stream, comprising a desorbent compound, through the first adsorptive separation zone and desorbing paraffinic hydrocarbons to produce a first extract stream comprising the normal and monomethyl paraffinic hydrocarbons and the desorbent compound;

(c) fractionating the first extract stream to recover a first extract product stream comprising normal and monomethyl branched paraffinic hydrocarbons and a second desorbent stream;

(d) passing at least a portion of the first extract product stream into a second adsorptive separation zone, which second separation zone contains a bed of a second selective adsorbent maintained at adsorptive separation promoting conditions, selectively retaining normal paraffinic hydrocarbons on at least a portion of the selective adsorbent, and recovering from the second adsorptive separation zone a second raffinate stream comprising monomethyl paraffinic hydrocarbons which were not selectively retained on the second bed of selective adsorbent;

(e) passing a third desorbent stream, comprising the same desorbent compound, through the second adsorptive separation zone and desorbing normal paraffinic hydrocarbons to produce a second extract stream comprising the normal paraffinic hydrocarbons and the desorbent compound;

(f) fractionating the second extract stream to recover the desorbent compound as a fourth desorbent stream; and (g) combining the second and fourth desorbent streams and using at least a portion of the resultant desorbent as the first desorbent stream.

* * * * *

UNITED STATES PATENT AND TRADEMARK OFFICE
CERTIFICATE OF CORRECTION

PATENT NO.    : 6,407,305 B1
DATED         : June 18, 2002
INVENTOR(S)   : Stephen W. Sohn et al.

It is certified that error appears in the above-identified patent and that said Letters Patent is hereby corrected as shown below:

<u>Title page,</u>
Item [75], Inventors ""Santi Kulprathipanja, Inverness, IL" and "James E. Rekoske, Glenview, IL" should be listed as the second and third inventors.

<u>Column 15,</u>
Line 6, the word -- of -- should be inserted between "bed" and "selective."
Lines 9 and 18, the word "paraffinic" was misspelled. It should read -- paraffinic -- instead of "parrafinic".
Line 63, the word -- and -- should be inserted between "desorbent" and "paraffinic."

Signed and Sealed this

Twenty-second Day of October, 2002

Attest:

*Attesting Officer*

JAMES E. ROGAN
*Director of the United States Patent and Trademark Office*